(12) United States Patent
Dasai et al.

(10) Patent No.: US 9,482,641 B2
(45) Date of Patent: Nov. 1, 2016

(54) DEVICE AND METHOD FOR DETECTING CHEMICAL AND PHYSICAL PHENOMENA

(75) Inventors: Fumihiro Dasai, Toyohashi (JP); Kazuaki Sawada, Toyohashi (JP); Hirokazu Nakazawa, Toyohashi (JP)

(73) Assignee: National University Corporation Toyohashi University of Technology (JP)

( * ) Notice: Subject to any disclaimer, the term of this patent is extended or adjusted under 35 U.S.C. 154(b) by 440 days.

(21) Appl. No.: 14/238,423

(22) PCT Filed: Aug. 9, 2012

(86) PCT No.: PCT/JP2012/070384
§ 371 (c)(1),
(2), (4) Date: Feb. 11, 2014

(87) PCT Pub. No.: WO2013/024791
PCT Pub. Date: Feb. 21, 2013

(65) Prior Publication Data
US 2014/0200842 A1    Jul. 17, 2014

(30) Foreign Application Priority Data

Aug. 12, 2011 (JP) .................................. 2011-176495

(51) Int. Cl.
*G01N 27/416* (2006.01)
*G01R 35/00* (2006.01)

(52) U.S. Cl.
CPC ......... *G01N 27/4165* (2013.01); *G01R 35/005* (2013.01)

(58) Field of Classification Search
CPC .......................... G01R 35/005; G01N 27/4165
USPC ................... 702/104; 377/57, 63; 422/82.01; 324/607, 678
See application file for complete search history.

(56) References Cited

U.S. PATENT DOCUMENTS 3,789,267 A * 1/1974 Krambeck ........... G11C 19/282
257/248
3,819,958 A * 6/1974 Gosney .................. G11C 27/04
257/245

(Continued)

FOREIGN PATENT DOCUMENTS

JP         11-201775 A       7/1999
JP       2005337806 A      12/2005

(Continued)

OTHER PUBLICATIONS

International Search Report for PCT/JP2012/070384 with English Translation.

(Continued)

*Primary Examiner* — Carol S Tsai
(74) *Attorney, Agent, or Firm* — Quarles & Brady LLP; Gavin J. Milczarek-Desai

(57) ABSTRACT

Provided is a device adapted for detecting chemical and physical phenomena and suitable for high integration, and a method for controlling the detection device. When a plurality of pH-detecting devices are used, a variation in sensitivity occurs in each of the sensing units. The variation in sensitivity can be calibrated using a simple method. The amount of charge (output signal) delivered by each of the sensing units to a standard solution is determined, and the difference between the delivered charge amount and a standard charge amount (standard output signal) delivered by a standard sensing unit is determined. The capacity of the potential well of the sensing unit is changed, or the potential of a TG unit when a charge is delivered is changed, so as to cancel out the difference.

13 Claims, 15 Drawing Sheets

(56) References Cited

U.S. PATENT DOCUMENTS

| | | | | |
|---|---|---|---|---|
| 3,987,475 A * | 10/1976 | Ibrahim | ................ | G11C 19/285 257/239 |
| 4,035,666 A * | 7/1977 | Collins | ................ | G06G 7/1907 257/251 |
| 4,039,940 A * | 8/1977 | Butler | ................ | G01R 27/2605 324/607 |
| 4,048,525 A * | 9/1977 | Goldberg | ................ | G11C 27/04 257/236 |
| 4,090,095 A * | 5/1978 | Herrmann | ......... | H01L 29/76816 257/239 |
| 4,187,460 A * | 2/1980 | Dauge | ................ | G01R 27/2605 324/607 |
| 4,360,745 A * | 11/1982 | Prince | ................ | H03K 17/145 257/237 |
| 6,294,133 B1 | 9/2001 | Sawada et al. | | |
| 6,515,703 B1 * | 2/2003 | Suzuki | ................ | H04N 5/355 348/312 |
| 6,998,195 B1 * | 2/2006 | Fjeldstad | ............ | G01B 11/164 359/3 |
| 7,218,903 B2 * | 5/2007 | Komatsu | ............ | H03G 3/3036 375/351 |
| 7,465,915 B2 | 12/2008 | Sawada et al. | | |
| 7,826,980 B2 | 11/2010 | Sawada et al. | | |
| 7,837,844 B2 * | 11/2010 | Patel | ................ | G01N 27/226 204/400 |
| 7,947,939 B2 * | 5/2011 | Schrey | ................ | H04N 5/3575 250/208.1 |
| 8,023,468 B2 | 9/2011 | Liu et al. | | |
| 8,168,120 B1 * | 5/2012 | Younis | ................ | G01N 29/022 422/68.1 |
| 8,427,177 B2 * | 4/2013 | Jeong | ................ | G01C 19/5719 324/658 |
| 8,501,097 B1 * | 8/2013 | Younis | ................ | G01N 29/022 422/50 |
| 9,000,364 B2 * | 4/2015 | Ermakov | ............ | H01J 49/4245 250/281 |
| 2005/0054311 A1 * | 3/2005 | Komatsu | ............. | H03G 3/3036 455/219 |
| 2005/0062093 A1 | 3/2005 | Sawada et al. | | |
| 2006/0237310 A1 * | 10/2006 | Patel | .................... | G01N 27/226 204/400 |
| 2007/0197177 A1 * | 8/2007 | Komatsu | ............ | H03G 3/3036 455/218 |
| 2008/0258044 A1 * | 10/2008 | Schrey | ................ | H04N 5/3575 250/208.1 |
| 2010/0084549 A1 * | 4/2010 | Ermakov | ............ | H01J 49/4245 250/283 |
| 2011/0101241 A1 * | 5/2011 | Cottier | ............. | H01L 27/14601 250/459.1 |
| 2011/0174987 A1 | 7/2011 | Sawada et al. | | |
| 2011/0236263 A1 | 9/2011 | Sawada et al. | | |
| 2012/0002201 A1 | 1/2012 | Sawada et al. | | |
| 2012/0270205 A1 * | 10/2012 | Patel | ................... | G01N 27/126 435/5 |

FOREIGN PATENT DOCUMENTS

| | | | |
|---|---|---|---|
| JP | 2006121151 A | | 5/2006 |
| JP | 2006284225 A | | 10/2006 |
| JP | 2006284250 A | * | 10/2006 |
| JP | 2006284250 A | | 10/2006 |
| JP | 4073831 B2 | | 2/2008 |
| JP | 200879306 A | | 4/2008 |
| JP | 4133028 B2 | | 6/2008 |
| JP | 471820 B2 | | 8/2008 |
| JP | 4183789 B2 | | 9/2008 |
| WO | 03042683 A1 | | 5/2003 |
| WO | 2007108465 A1 | | 9/2007 |
| WO | 2009081890 A1 | | 7/2009 |
| WO | 2009151004 A1 | | 12/2009 |
| WO | 2010106800 A1 | | 9/2010 |

OTHER PUBLICATIONS

Written Opinion for PCT/JP2012/070384 with English Translation.

* cited by examiner

DEVICE AND METHOD FOR DETECTING CHEMICAL AND PHYSICAL PHENOMENA

FIELD OF THE INVENTION

The present invention relates to improvements in a chemical and physical phenomenon detecting device and a method for detecting a chemical and physical phenomenon.

BACKGROUND OF THE INVENTION

As to a chemical and physical phenomenon detecting device which is sometimes referred to as "a detecting device" hereinafter, the detecting device utilizing a floating diffusion which is sometimes referred to as "a FD section" hereinafter has been proposed as referred to patent documents 1-8.

For example, as shown in FIG. 1, such a detecting device is provided with a sensing section 10, a charge supply section 20, a charge transfer storage section 30, a charge quantity detecting section 40 and a charge eliminating section 50.

The sensing section 10 is provided with a sensing film 12 for changing a potential correspondingly to a detected object and a reference electrode 13. In accordance with the potential change of the sensing film 12, the depth of the potential well 15 is changed in a region, namely a p-type diffusion region 72 of a silicon substrate 71 faced with the sensing film 12.

The charge supply section 20 is provided with an injection diode section 21 sometimes referred to as "ID section" hereinafter and an input control gate section 23 sometimes referred to as "ICG section" hereinafter. The ID section 21 is charged with a charge. Then, with the potential of the ICG section 23 controlled, the charge in the ID section 21 is transferred to the potential well 15 of the sensing section 10.

The charge transfer storage section 30 is provided with a transfer gate section 31 sometimes referred to as "a TG section" hereinafter and a floating diffusion section 33 sometimes referred to as "an FD section". With the voltage of the TG section 31 controlled to change a potential of a region of the silicon substrate 71 which is faced with the TG section 31, the charge charged in the potential well 15 of the sensing section 10 is transferred to the FD section 33 and stored in the FD section 33.

The charge stored in the FD section 33 is detected by a charge quantity detecting section 40. As such a charge quantity detecting section 40, a source follower type signal amplifier can be used.

The charge eliminating section 50 is provided with a reset gate section 51 sometimes referred to as "a RG section" and a reset drain section 53 sometimes referred to as "a RD section". With the voltage of the RG section 51 controlled to change a potential of a region of the silicon substrate 71 which is faced with the RG section 51, the charge stored in the FD section 33 is transferred to the RD section 53 and discharged from the RD section 53.

The detailed structure and the behavior of such the detecting device are explained in the following by referring to a pH sensor for detecting the concentration of hydrogen ions as an example. As explained in the following, an electron is used as a charge. The subject region of the substrate 71 is doped suitably for transferring the electron.

The detecting device used for the pH sensor has an n-type silicon substrate 71. A part of the silicon substrate 71 corresponding to the sensing section 10 is made a p-type diffusion region 72. The surface of the p-type diffusion region 72 is doped to form an n-type region 73.

In the ID section 21, the FD section 33 and the RD section 53 of the silicon substrate 71, n+ regions 74, 75 and 77 are formed respectively.

On the surface of the silicon substrate 71, a protective film 81 made of silicon oxide is formed. On the protective film 81, the electrode of the ICG section 23, the electrode of the TG section 31 and the electrode of the RG section 51 are put. If each of the electrodes are applied with voltage, the potential of each region of the silicon substrate 71 faced with each of the electrodes is changed.

In the sensing section 10, the sensing film 12 made of silicon nitride is put on the protective film 81.

As referred to FIG. 2, the basic behavior of the detecting device 1 is explained in the following.

If a solution which is a detected object contacts the sensing section 10, the depth of the potential well 15 of the sensing section 10 changes in accordance with the concentration of hydrogen ions, as referred to the step (A). Namely, the larger the concentration of hydrogen ions becomes, the deeper the potential well 15 becomes. In other words, the bottom of the potential becomes high.

On the other hand, the ID section 21 is charged with a charge by lowering the potential of the ID section 21, as referred to the step (B). At the same time, the charge charged in the ID section 21 overflows the ICG section 23 to fill the potential well 15 of the sensing section 10. By the way, the potential of the TG section 31 is lower than the potential of the ICG section 23. So, the charge charged in the potential well 15 does not overleap the TG section 31 to reach the FD section 33.

Next, with the potential of the ID section 21 increased, the charge is extracted from the ID section 21. The charge slashed off by the ICG section 23 is left in the potential well 15, as referred to the step (C). Here, the charge quantity left in the potential well 15 corresponds to the depth of the potential well 15, namely the concentration of hydrogen ions which is the detected object.

Next, with the potential of the TG section 31 increased, the charge left in the potential well 15 is transferred to the FD section 33, as referred to the step (D). Thus, the charge stored in the FD section 33 is detected by the charge quantity detecting section 40, as referred to the step (E). Then, with the potential of the RG section 51 increased, the charge of the FD section 33 is evacuated to the RD section 53, as referred to the step (F). The RD section 53 is connected to VDD which absorbs the negative charge.

The circuit configuration of the pH detecting device of FIG. 1 is shown in FIG. 3. The charge in the FD section is converted into the voltage signal by a source follower circuit so that the voltage signal is outputted as the output signal from the output line OUT.

RELATED ART DOCUMENT

Patent document

Patent document 1: JP-B-4171820
Patent document 2: JP-A-2008-79306
Patent document 3: JP-B-4073831
Patent document 4: JP-B-4183789
Patent document 5: JP-B-4133028
Patent document 6: WO/2009/081890A1
Patent document 7: WO/2010/106800A1
Patent document 8: WO/2009/151004A1

DISCLOSURE OF THE INVENTION

Problems to be Solved by the Invention

The pH detecting device described above has a constitution that various electrodes and a sensing film are formed on a silicon substrate. So, the pH detecting device can be integrated into a two-dimensional device which can detect two-dimensional pH distribution to output the two-dimensional pH distribution as an image.

Informing such an image, since each of the pH detecting devices corresponds to one pixel, highly-integrated pH detecting devices are required.

When plural detecting devices are used, the variation of the sensitivity is produced in each of the sensing sections. The cause for the variation in sensitivity is attributed to the fact that the sensing film is charged up, for example.

In general, for calibrating the variation in sensitivity, the output signal is obtained as to the standard solution in each of the sensing sections. Such the output signal is calibrated to the exact output signal by the software data processing. However, if the number of the sensing sections increases, the burden imposed on the computer becomes large to prevent the high integration of the device.

Means for Solving the Problems

So, the inventors of the present invention conceived the idea for calibrating the variation in sensitivity by hardware processing. Namely, the transferred charge quantity as to the standard solution in each of the sensing sections is obtained as the output signal. Next, the difference between such the transferred charge quantity and the standard transferred charge quantity as the standard output signal of the standard sensing section is obtained. Here, the standard sensing section can be selected arbitrarily or theoretically. The charge quantity transferred from the sensing section in contact with the standard solution is uniquely defined as standard transferred charge quantity and used as standard output of all of the sensing sections.

The capacitance of the potential well of the sensing section is changed, or the potential of TG section for transferring the charge is changed, so as to cancel the difference between the standard transferred charge quantity and the transferred charge quantity of each of the sensing sections. Accordingly, the same charge quantity as the charge quantity transferred as to the standard solution from the standard sensing section to the FD section is transferred from the calibrated sensing section to the FD section.

The first aspect of the present invention is derived from the disclosure above and defined as the following.

Namely, a method for controlling a chemical and physical phenomenon detecting device provided with a first sensing section and a second sensing section for changing each bottom potential of each potential well correspondingly to a chemical and physical phenomenon which is to be detected, the chemical and physical phenomenon detecting device transferring a charge of each of the sensing sections to an FD section corresponding to each of the sensing sections through a TG section for identifying the chemical and physical phenomenon on a basis of a charge stored in the FD section, comprising the steps of:

changing a capacitance of a potential well of at least one of the first sensing section and the second sensing section for detecting the chemical and physical phenomenon, and/or changing a potential of the TG section for transferring the charge; and transferring a first quantity of charges from a first potential well of the first sensing section and a second potential well of the second sensing section to the FD section correspondingly to the first sensing section and the second sensing section, when the chemical and physical phenomenon is in a first state of the chemical and physical phenomenon.

According to the first aspect of the control method thus defined, correspondingly to the same chemical and physical phenomenon (the first state), a charge of the same quantity (the first quantity) is transferred from the first and the second sensing sections to the FD section. Here, the transferred charge quantity (the first quantity) is adjusted by the hardware method so-called, namely the method for changing the capacitance of the potential well of the sensing section and/or the potential of the TG section. Accordingly, the burden imposed on the data processing is small. Even if the number of the integrated detecting devices increases, the data processing can substantially be executed in real time.

EMBODIMENTS

Figure 1:
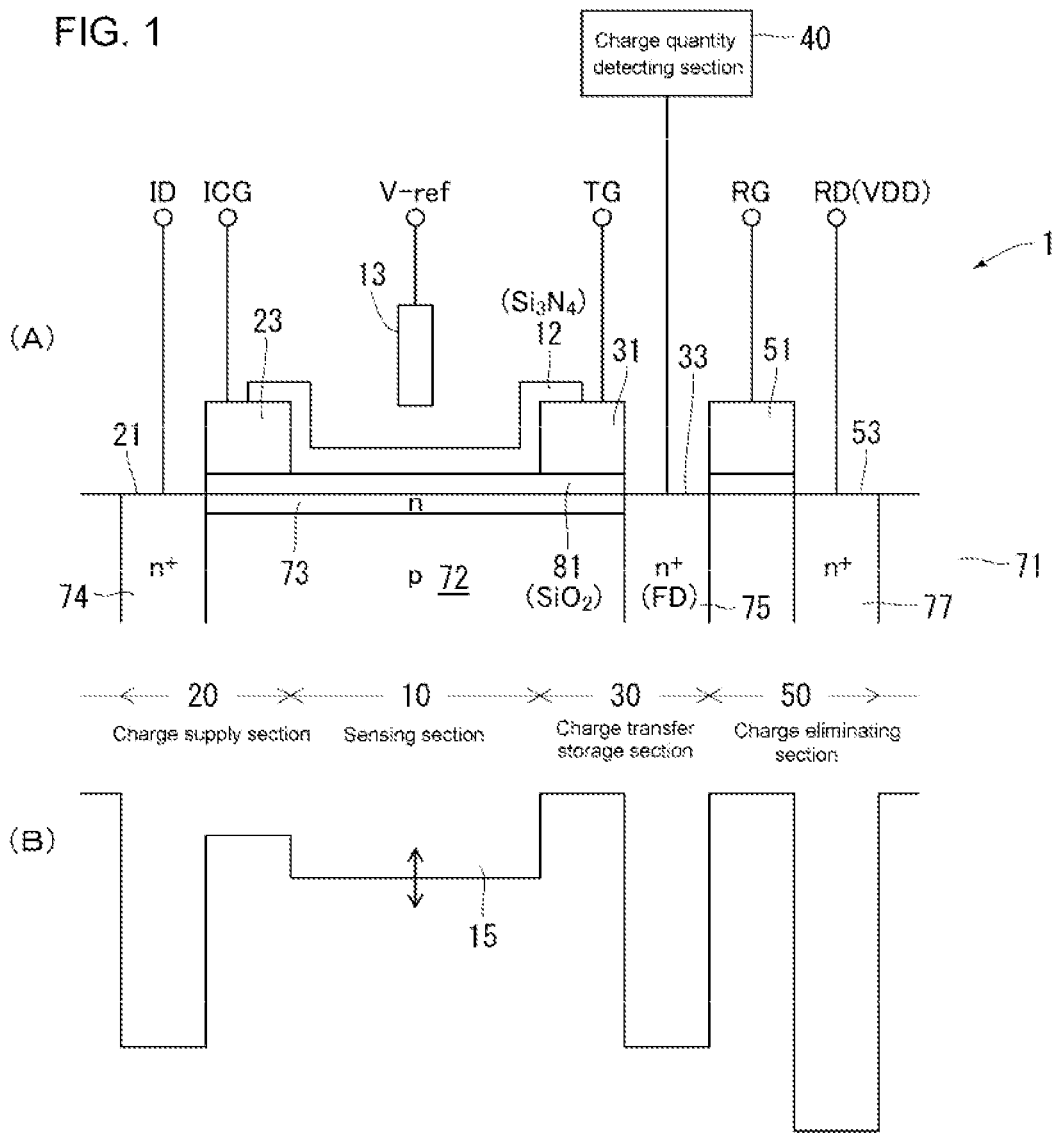
FIG. 1 shows a schematic configuration of a conventional detecting device.

An embodiment of the present invention is explained in the following by referring to an example of integrated pH detecting devices 1 which have a structure shown in FIG. 1.

Figure 4:
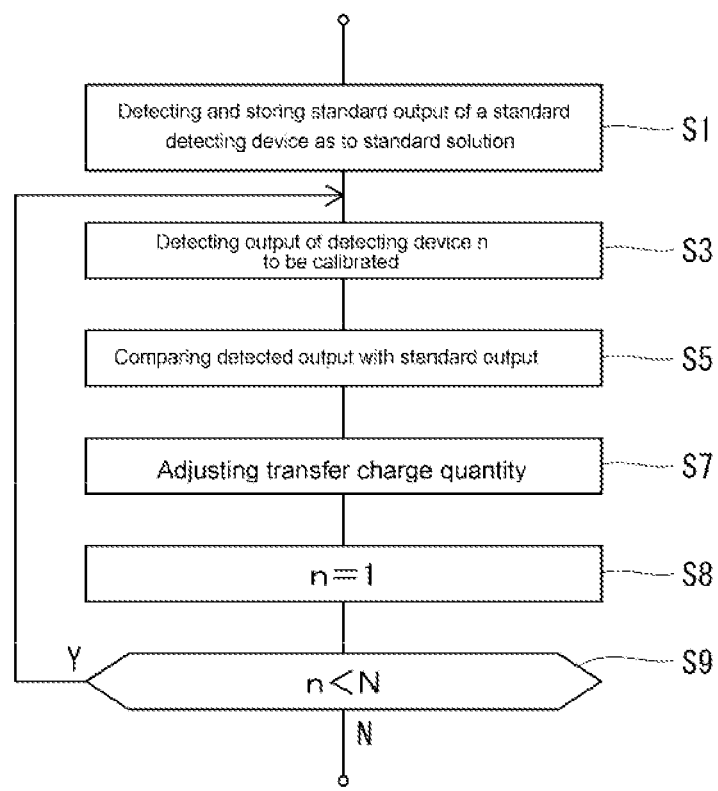
FIG. 4 is the flowchart showing an operation of the detecting device shown in FIG. 1.
Figure 5:
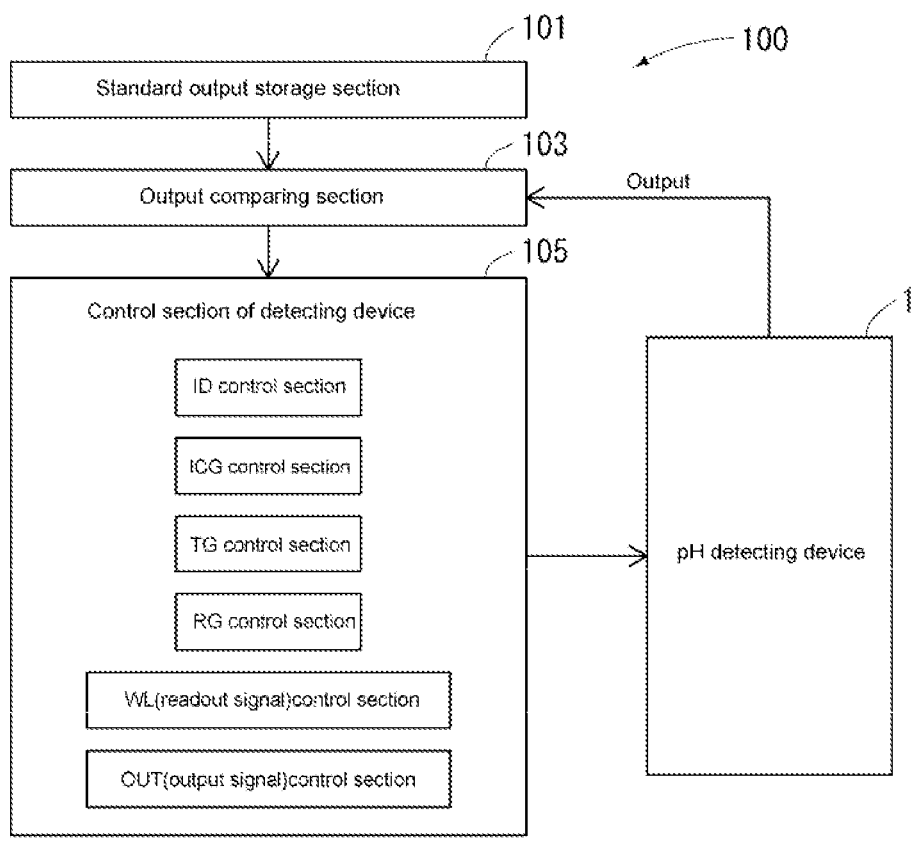
FIG. 5 is a block diagram showing a configuration of a calibrating device.

In the present invention, the output of the integrated pH detecting devices 1 is efficiently calibrated. First, as shown in the step S1 of FIG. 4, the standard output of the standard pH detecting device is identified as to the standard solution and stored in a standard output storage section 101. The standard output of the standard pH detecting device is sometimes referred to as "standard output" hereinafter. By the way, in FIG. 5, a calibrating device 100 of the embodiment of the present invention is shown.

Incidentally, the output of the pH detecting device corresponds to the charge quantity which is transferred from the sensing section 10 to the FD section 33. Each of the pH detecting devices including the standard pH detecting device has the same physical structure in the view of design. Namely, in theory, when the standard solution is detected, the potential well 15 of the sensing section 10 of each of the pH detecting devices has the same depth. So, in each of the pH detecting devices, the charge quantity transferred from the potential well to the FD section 33 is also the same in theory. However, in fact, in each of the pH detecting devices, the output has a different value as described above.

In the step S3, the output of the pH detecting device 1 which is to be calibrated is detected. In an output comparison section 103, the detected output and the standard output are compared, as referred to the step S5.

In the step S7, on a basis of the comparison result in the step S5, the voltages applied to the respective elements of the pH detecting device 1 which is to be calibrated are changed so as to make the output of the pH detecting device 1 which is to be calibrated on the standard solution equal to the standard output. The detail of the step S7 is described below.

The processes in the steps S5 and S7 are executed on all of the N pieces of pH detecting devices which are to be integrated, as referred to the steps S8 and S9.

Next, the detail of the step S7 is explained in the following.

The following methods (A) and/or (B) can be adopted as the calibration method for making the output for the standard solution equal to the standard output in the pH detecting device which is to be calibrated.

In the method (A), the capacitance of the potential well 15 of the sensing section 10 is adjusted.

In the method (B), the charge quantity transferred from the potential well 15 to the FD section 33 is adjusted by changing the potential of the TG section 31.

Incidentally, in the detection of the chemical quantity or the physical quantity, when the detected quantity changes according to the sensing period, the detecting device can be calibrated by adjusting the sensing period.

As described above, in the method (A), the capacitance of the potential well 15 of the sensing section 10 is adjusted.

Namely, the capacitance of the potential well 15 of the sensing section 10 can be adjusted by changing the height of the potential barrier which constitutes the potential well 15. As to such the potential barrier, the capacitance of the potential well 15 is defined by the minimum height of such the potential barrier. The charge of the potential well 15 beyond the minimum height cannot be detected because the charge beyond the minimum height overflows the potential well 15.

The potential barrier, especially the minimum height of the potential barrier constituting the potential well 15 can be adjusted by the ICG section 23 and the TG section 31. For evacuating the charge of the potential well 15, the potential of the ICG section 23 is preferably made higher than that of the TG section 31. When the charge of the potential well 15 is evacuated from the TG section 31, the evacuated charge 15 is stored in the FD section 33. So, before the detection is performed, it is necessary to cancel the charge.

Another electrode is provided adjacently to the sensing section. The minimum height of the potential barrier constituting the potential well of the sensing section can be controlled by changing the potential of such another electrode.

Figure 6:
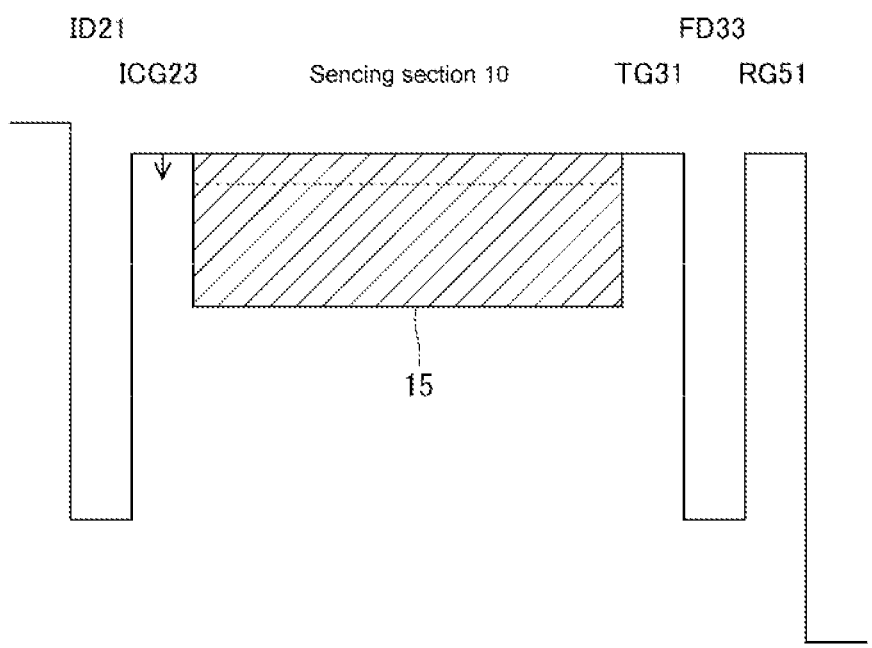
FIG. 6 is a pattern diagram showing an example of making the capacitance of the potential well the same as that of the standard pH detecting device shown by the dotted line by increasing the potential of the ICG section in the sensing period.

In the example of FIG. 6, the potential of the ICG section 23 is increased so that the capacitance of the potential well 15 becomes the same as that of the standard pH detecting device shown by the dotted line in FIG. 6.

When the capacitance of the potential well 15 of the pH detecting device which is to be calibrated is larger than the capacitance of the potential well 15 of the standard pH detecting device, it is required to increase the potential of either the ICG section 23 or the TG section 31. So, the processes can be simplified.

For executing such the simplified processes, the capacitance of the potential well 15 of the standard pH detecting device is preferred to be less than the capacitance of the potential well 15 of all of the pH detecting devices which are to be calibrated. For this object, the outputs, namely the transferred charge quantities of all of the integrated pH detecting devices are detected. Then, the pH detecting device with the minimum output is selected as the standard pH detecting device, and the minimum output is selected as the standard output.

The capacitance of the potential well 15 may be adjusted by the bottom potential of the potential well. The bottom potential of the potential well 15 can be controlled by the standard electrode 13.

As described above, in the method (B), the charge quantity transferred from the potential well 15 to the FD section 33 is adjusted by changing the potential of the TG section.

In general, when the charge of the potential well 15 is transferred to the FD section 33, the potential of the TG section 31 is made higher than the potential of the bottom of the potential well 15 to transfer all of the charges of the potential 15 to the FD section 33.

On the other hand, the potential of the TG section is made lower than the potential of the bottom of the potential well to control the transferred quantity of the charge.

Figure 7:
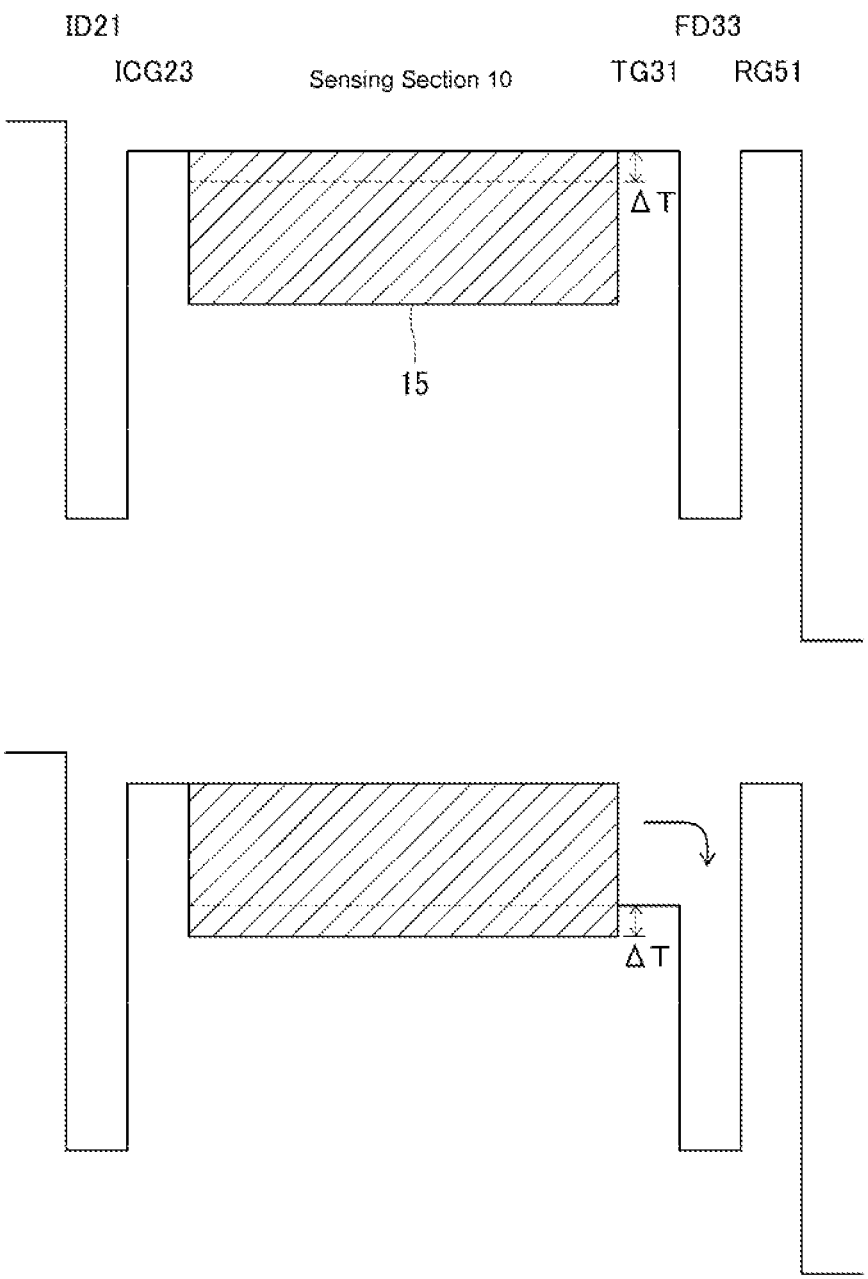
FIG. 7 is a pattern diagram showing an example of adjusting the charge quantity transferred from the potential well to the FD section by adjusting the potential of the TG section.

In the example of FIG. 7, the capacitance of the potential well of the standard pH detecting device is shown by the dotted line. The potential difference corresponding to the capacitance difference between the capacitance of the potential well of the standard pH detecting device and the capacitance of the potential well 15 of the pH detecting device to be calibrated is defined as $\Delta T$. In such a case, when the charge is transferred, the minimum potential of the TG section is made lower than the bottom potential of the potential well 15 by $\Delta T$ to transfer the same charge quantity as that of the standard pH detecting device.

In such the example, the capacitance of the potential well of the standard pH detecting device is required less than the capacitance of the potential well 15 of the pH detecting device which is to be calibrated. So, the outputs, namely the charge quantities of all of the integrated pH detecting devices are detected. In such the example, the minimum value of the output is preferably defined as the output, namely the standard output of the pH detecting device.

In the example described above, the output of the PH detecting device to be calibrated is calibrated by referring to the standard output.

However, according to the sensitivity required for the pH detecting device, it is not necessary to calibrate the output of each of the pH detecting devices individually. For example, the difference between the output (transferred charge quantity) of sensing section to be calibrated and the standard output (standard transferred charge quantity) is classified into predetermined ranges (charge quantity ranges). In addition, the calibration value is determined per predetermine range in advance. Then, the capacitance of the potential well to be calibrated is calibrated by the calibration value. As described above, the hardware adjusting operation can be simplified.

Figure 8:
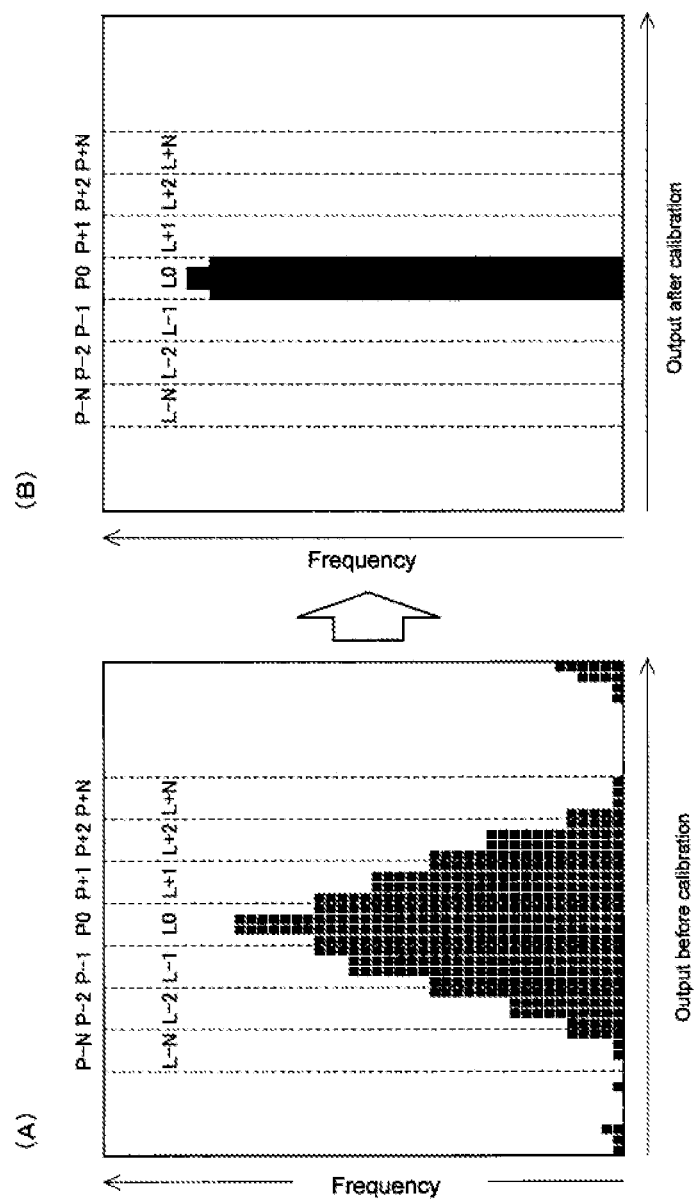
FIG. 8 is diagram for explaining the principle of the method of calibrating the output of the pH detecting device.

FIG. 8(A) shows the output distribution of the integrated pH detecting devices as to the standard solution before calibration. In the example of FIG. 8(A), the outputs of the integrated pH detecting devices are classified into the predetermined widths of the output ranges.

In such the example, the central value P0 of the central output range L0 is defined as the standard output. Next, the differences $\Delta p \pm 1$, $p \pm N$ between the standard output P0 and the respective central values $P \pm n$ of the respective output ranges $L \pm n$ are obtained. Then, the variation value of the capacitance of the potential well is identified according to the respective differences. Further, the capacitance of the potential well of the pH detecting devices which output all of the outputs included in the output ranges $L \pm n$ is adjusted correspondingly to the difference $\Delta p \pm N$ between the standard output P0 and the central value $P \pm n$ of the output range $L \pm n$. As the adjusting method, the potential adjustment of the ICG section 23 may be adopted.

Such the adjusted data is shown in FIG. 8(B). As shown in FIG. 8(B), the outputs of the integrated pH detecting devices are distributed within a predetermined width.

The following modified embodiment may be adopted for improving the detecting sensitivity, the detecting rate and the device integration of the detecting device.

(The Sensing Section)

Figure 2:
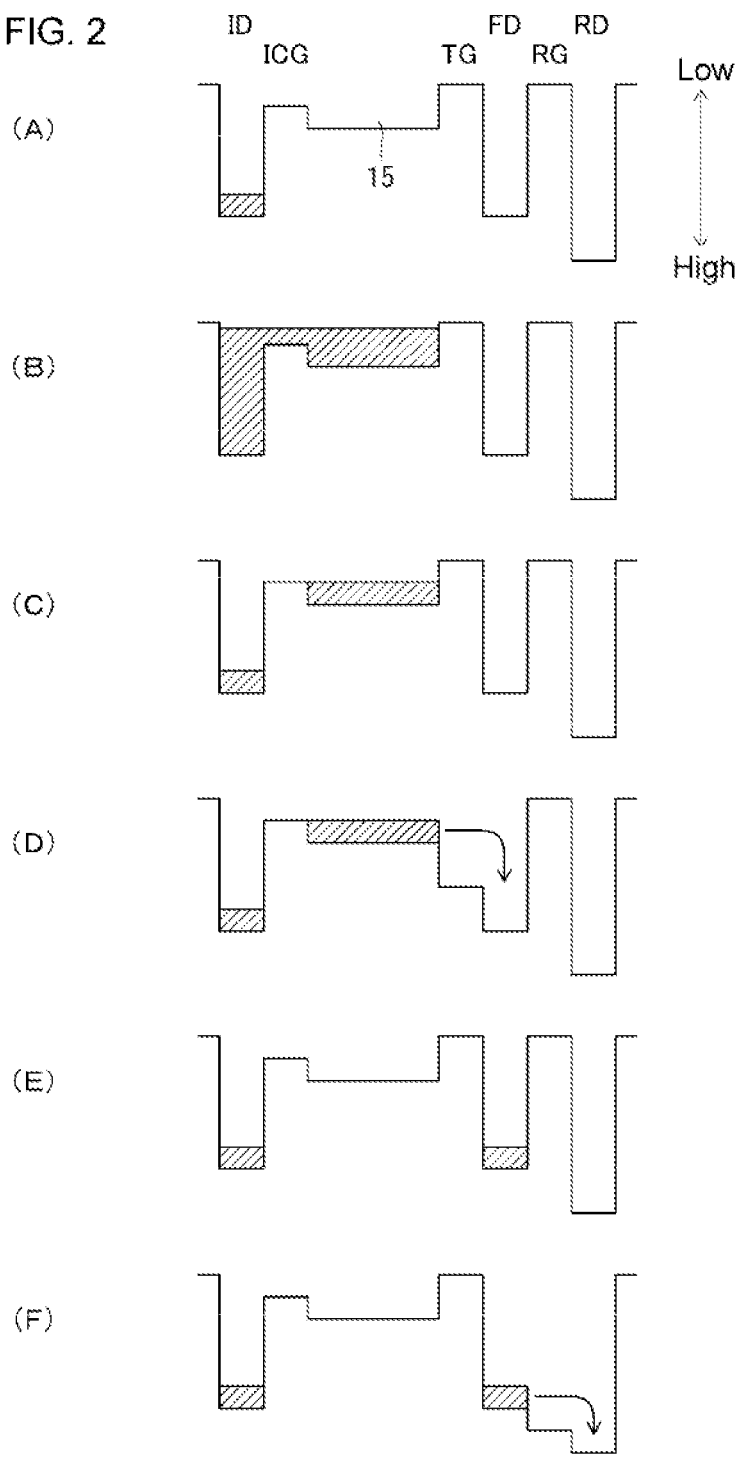
FIG. 2 is an operation flow of the conventional detecting device.

For improving the detecting sensitivity, the steps (A)-(D) of FIG. 2 are repeated to detect the charge quantity cumulatively accumulated in the FD section 33, as referred to Japanese Patent JP-B-3623728.

On the other hand, when the charge is slashed off by the ICG section 23, as referred to the step (C) of FIG. 2, the small potential bump may be formed in the interface between the ICG section 23 and the potential well 15 correspondingly to the width of the sensing film 12. If such the potential bump is formed, the redundant charge is left in the sensing section correspondingly to the height of the potential bump. Even if the height of the potential bump is small, in case that the detecting operations are cumulatively repeated, the charge quantity left due to the potential bump cannot be ignored.

So, the eliminating well is formed adjacently to the sensing section or within the sensing section, so that the charge left in the sensing section due to the potential bump is evacuated to the eliminating well. In such a way, the charge quantity transferred from the sensing section to the FD section corresponds exactly to the pH value. Namely, the charge left due to the potential bump is not transferred so that the exact detection can be executed.

Incidentally, the control electrode for controlling the potential of the eliminating electrode is further provided correspondingly to the eliminating well. Such the control electrode is controlled independently of the ICG section and the TG section.

The description above is referred to Japanese patent JP-B-4171820.

(Charge Supply Section)

Figure 9:
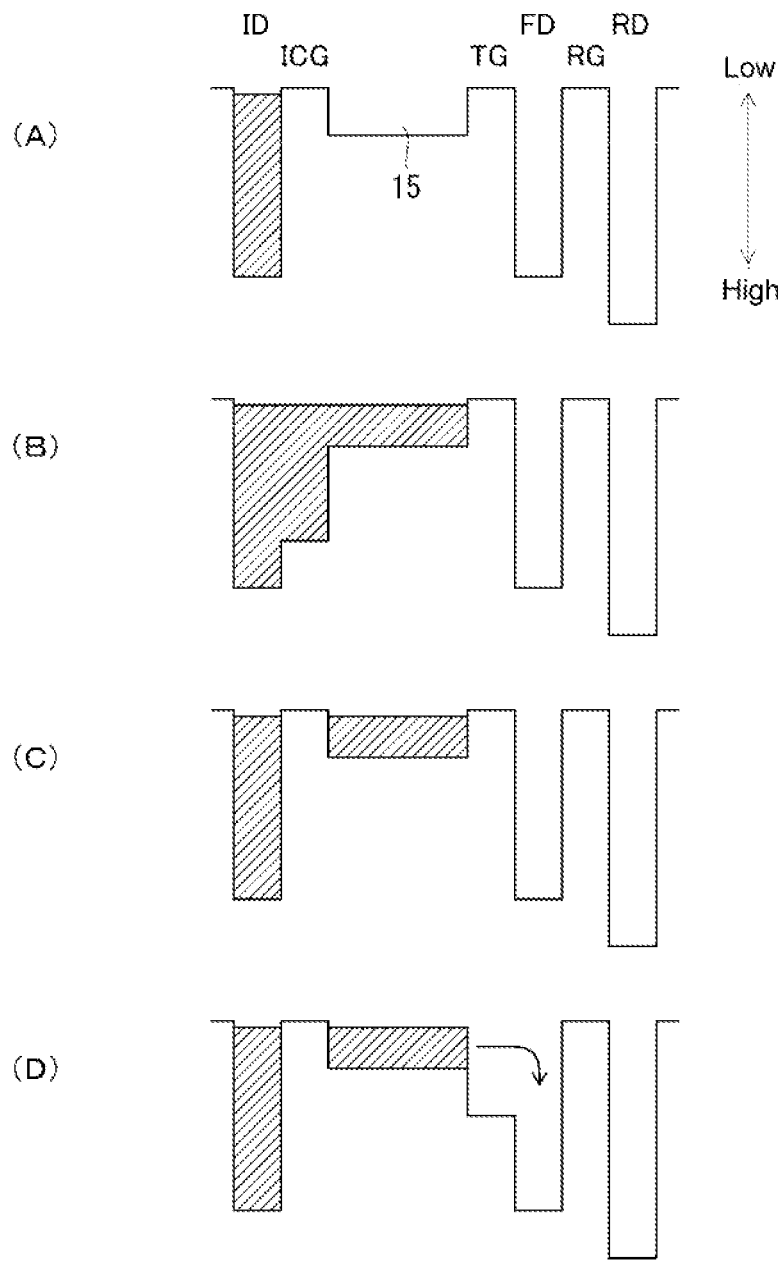
FIG. 9 is an operation flow of another example of the charge supply.

Another method for supplying the charge is explained by referring to FIG. 9.

In an example of FIG. 9, the ID section 21 is always charged with the charge. Then, the lowest potential of the charge is lower than the possibly lowest potential of the potential well 15 and is higher than the lowest potential of the TG section 31, as referred to the (A) of FIG. 9.

Next, the potential of the ICG section 23 is set higher than the bottom potential of the potential well 15 to fill the potential well 15 with the charge of the ID section 21, as referred to the step (B) of FIG. 9. Incidentally, the ID section 21 is always placed in condition for supplying the charge to keep the lowest potential of the charge.

Next, the potential of the ICG section 23 is set low enough to breakup the charge into the charge of the ID section 21 and the charge of potential well 15 by the ICG section 23, as referred to the step (C) of FIG. 9. Then, the potential of the TG section 31 is increased to transfer the charge of the potential well 15 to the FD section 33, as referred to the step (D) of FIG. 9.

Incidentally, the charge detection and the charge evacuation in the FD section are executed in the processes similar to the steps (E) and (F) of FIG. 2.

In the method for supplying the charge shown in FIG. 9, the slash off operation in the steps (B) and (C) of FIG. 2 is not included. So, the method shown in FIG. 9 can eliminate the effect caused by the potential bump.

In addition, the operation for increasing and decreasing the potential of the ICG section 23 can be executed more rapidly than the method of FIG. 2 which necessitates the operations for charging and discharging the ID section 21. The inventors conceive that the period required for the steps (B) and (C) of FIG. 9 which separate the charge of the ID section 21 and the charge of the potential well 15 can be reduced between ½ and ⅕ of the period required for the steps (B) and (C) of FIG. 2 which slash off the charge.

Incidentally, the electrode of the ICG section 23 is preferred to introduce the potential gradient which is higher in the ID section 21 side and lower in the sensing section 10 side so that the charge faced with the electrode of the ICG section 23 is preferably transferred to the ID section side 21 more rapidly.

Figure 10:
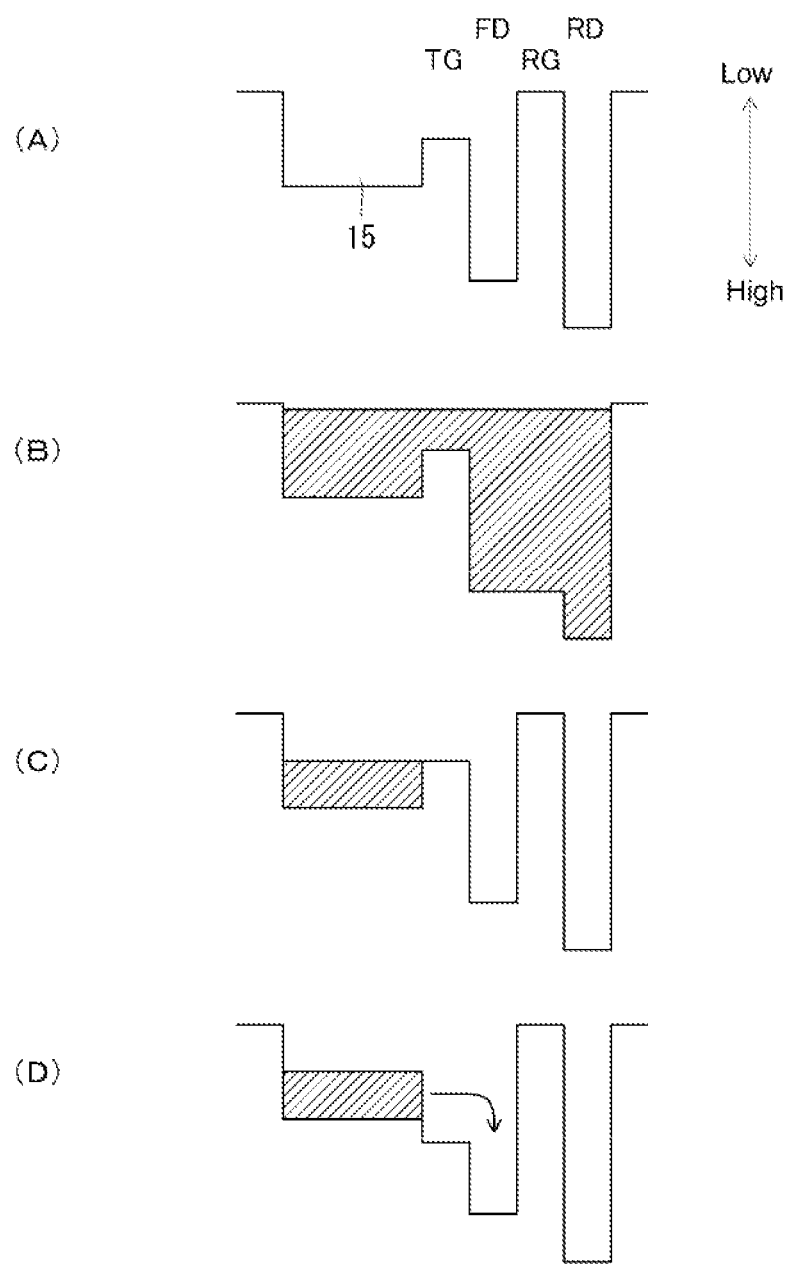
FIG. 10 is an operation flow of another example of the charge supply.

In FIG. 10, another method for supplying the charge is shown.

In such a method for supplying the charge, the charge supply section 20 is eliminated from the detecting device. The charge is supplied from the FD section 33 in place of the charge supply section 20.

In the step (A) of FIG. 10, the potential of the potential well 15 is determined correspondingly to a pH value which is to be detected.

Then, while the potential of the RG section 51 is made high, the RD section 53 is charged with the charge. The lowest potential of the charge is made lower than the possibly lowest potential of the potential well 15. So, the potential well 15 is filled with the charge from the RD section 53, as referred to the step (B) of FIG. 10.

Next, the charge is evacuated from the RD section 53 to slash off the charge and to leave the charge only in the potential well 15. Then, the potential of the RG section 51 is retrieved, as referred to the step (c) of FIG. 10. Then, the potential of the TG section 31 is raised to transfer the charge left in the potential well 15 to the FD section 33, as referred to the step (D) of FIG. 10.

Incidentally, the charge detection and the charge evacuation in the FD section 33 are executed in the processes similar to the steps (E) and (F) of FIG. 2.

The device shown in FIG. 10 is not provided with the charge supply section which has independent constitution. The charge transfer storage section and the charge evacuating section work as the charge supply section. So, the device becomes simplified and suited for high integration.

Both of the sensing film 12 formed of silicon nitride and the protective film 81 formed of silicon oxide used for detecting pH as chemical quantity are translucent. So, when the sensing section 10 is used in the open space and so forth, the light which passes through these films 12, 81 produces the charge (electron) in the silicon substrate 71. If such the charge is stored in the FD section 33 together with the charge supplied from the charge supply section 20 to the sensing section 10, such the charge could cause the detection error.

So, the detecting device is provided with the means for adjusting the potential of the TG section 31 so as to transfer the charge from the sensing section 10 to the FD section 33 and detecting and storing the first charge quantity in condition that the charge is not supplied from the charge supply section 20 to the sensing section 10, and the means for adjusting the potential of the TG section 31 so as to transfer the charge of the sensing section 2 to the FD section 33 and detecting and storing the second charge quantity transferred to the FD section 33 in condition that the charge is supplied from the charge supply section 20 to the sensing section 10. The difference between the second charge quantity and the first charge quantity is calculated to correct the output of the detecting device on a basis of the obtained difference of the charge quantity. Accordingly, the influence of the light can be eliminated from the detected result of the detecting device.

The description above is referred to Japanese patent publication JP-A-2008-79306.

(Light Detection)

The light quantity can be detected by utilizing the fact that the sensing section 10 is activated for the light.

Namely, the light is produced in the sensing section 10 by irradiating the light. Then, by controlling the timing for transferring such the charge to the FD section 33, the light quantity irradiated on the sensing section 10 can be identified. In this case, the charge supply section 20 is not necessary.

Incidentally, the translucent electrode film is preferably stacked on the sensing section for the spectroscopic detection disclosed in Japanese patent JP-B-4073831. On the other hand, if the translucent electrode film is stacked on the sensing film, the sensing film does not contact the detected object, which makes the pH detection impossible.

(pH and Light Detection)

The light quantity can be detected by utilizing the basic structure of the pH detecting device. So, by introducing the time difference into the detection, both of pH and the light quantity can be detected by one chip, as referred to Japanese patent JP-B-4183789.

The charge transfer and storage section may be arranged respectively for pH detection and light detection, as referred to Japanese patent JP-B-4133028.

The device which can detect pH and the light quantity simultaneously is disclosed in WO/2009/081890A1. In such the device, the charge transfer and storage section for detecting pH by utilizing the electron as the charge and the charge transfer and storage section for detecting the light quantity by utilizing the hole generated by the light irradiation in the sensing section are provided together.

The spectroscopic device and its basic operation are disclosed in Japanese patent JP-B-4073831. In such the spectroscopic device, without the translucent electrode, the control of the potential of the TG section 23 produces the same condition as the potential applied to the sensing section is changed, as referred to WO/2010/106800A1.

Such the spectroscopic device is configured as the following. Namely, the spectroscopic device is provided with the sensing section for generating the charge by the incident light, the charge generation control section for controlling the sensing section between the first state capturing the charge generated from the surface to the first depth of the sensing section and the second state capturing the charge generated from the surface to the second depth of the sensing section, and the FD section for outputting the signal according to the charge quantity captured by the charge generation control section.

The charge generation control section is provided adjacently to the sensing section.

In addition, the spectroscopic device is provided with the TG section for defining the lowest potential of the charge filled in the potential well of the sensing section. With the potential of the TG section controlled, the lowest potential of the charge filled in the potential well is controlled to place the sensing section between the first state and the second state. The charge generated by the incident light overflows the gate section so that the charge is transferred to the FD section. The potential of the TG section is preferred higher than that of the ICG section.

In such the spectroscopic device, for analyzing the exciting light and the light including the fluorescence excited by the exciting light through spectroscopy, the first FD section and the second FD section are provided in order from the side of the sensing section. The capacitance of the first FD is larger than that of the second FD. The first FD is always filled in full with the charge transferred from the sensing section. The charge passing through the first FD is stored in the second FD section. The intensity of each light is identified by the charge quantity stored in the second FD section. Since the capacitance of the second FD section is small, the detection sensitivity can be improved.

The description above is referred to WO/2009/151004.

(Circuit Configuration)

Figure 11:
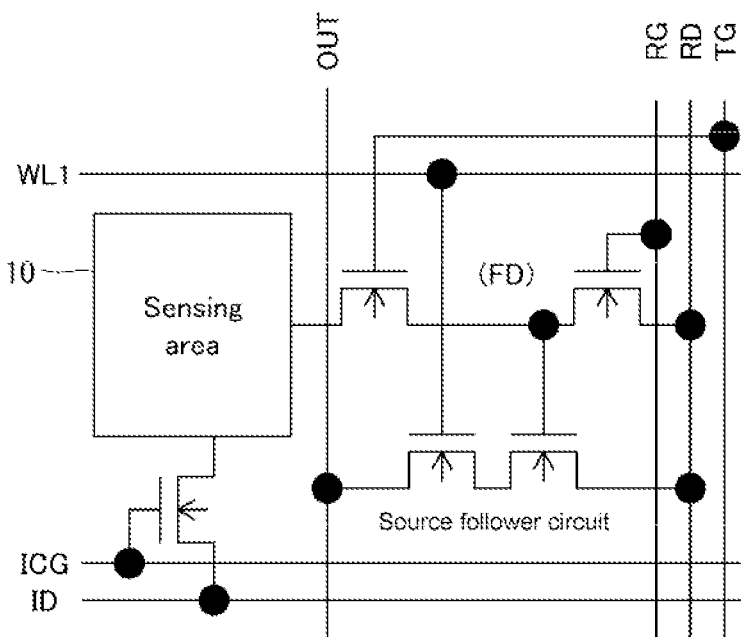
FIG. 11 is a basic circuit diagram of the pH detecting device.

The basic circuit configuration of the pH detecting device is shown in FIG. 11.

Figure 3:
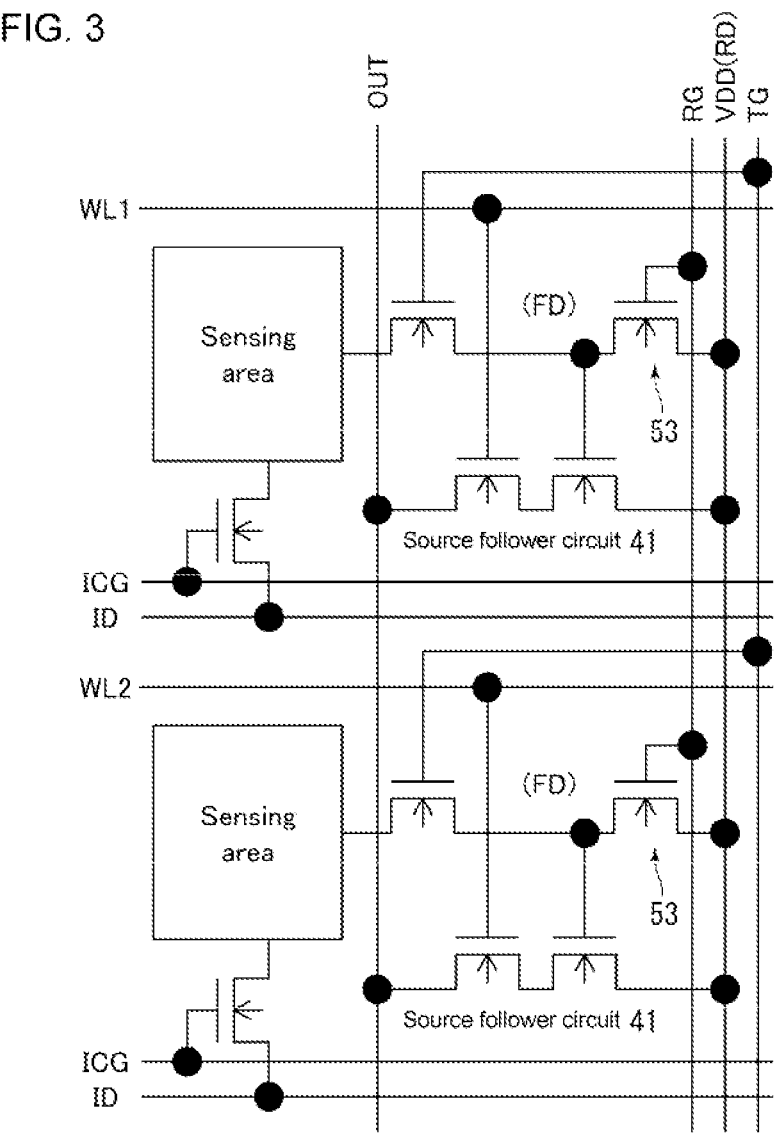
FIG. 3 is the wiring diagram of the detecting device shown in FIG. 1.

As shown in FIG. 11, for working a unitary detecting device sometimes referred to as "one pixel", five transistors and seven wirings are necessary for one sensing section. When the time lag is set between the pH detection and the light quantity detection, both of the pH and the light quantity can be detected by the circuit shown in FIG. 3.

Figure 12:
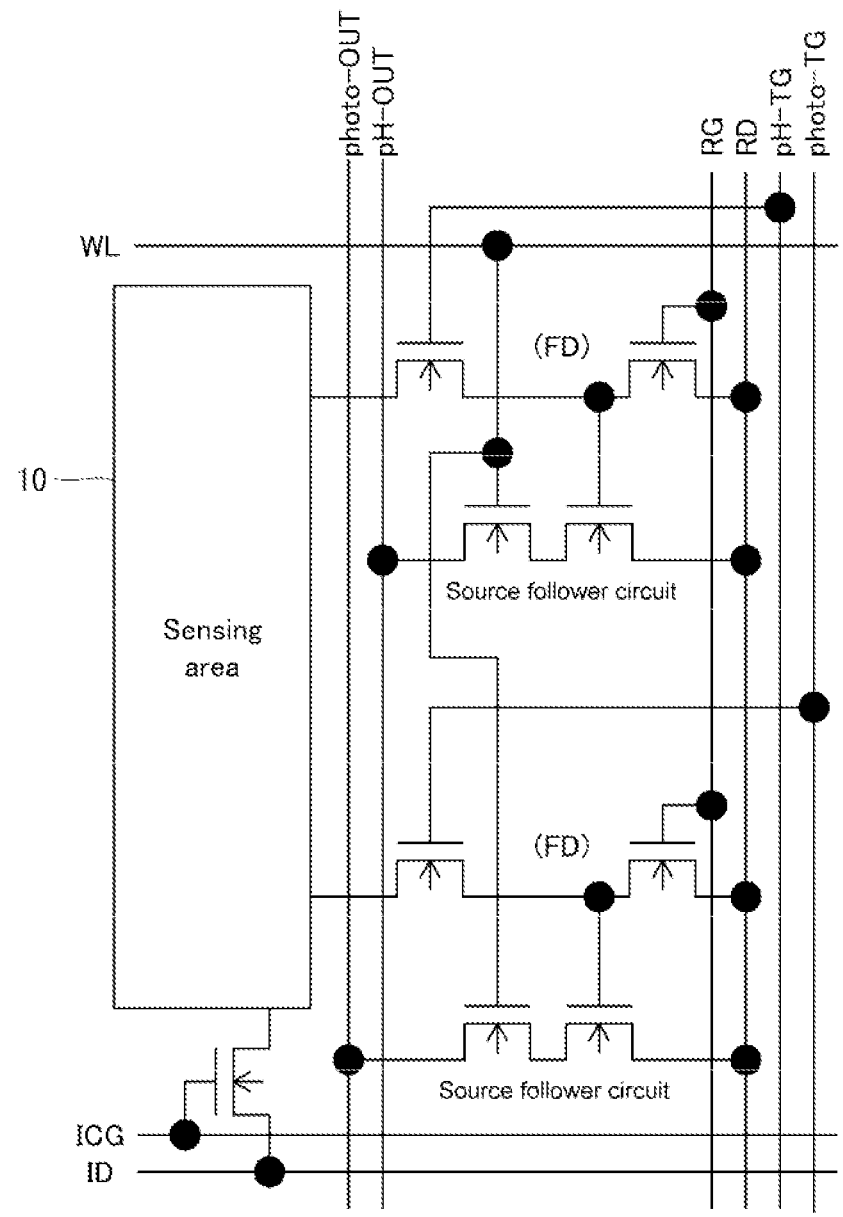
FIG. 12 is a circuit diagram of the charge transfer storage section for detecting pH which is provided with the charge transfer storage section for detecting light quantity.

The circuit configuration that the charge transfer storage section for detecting the pH and the charge transfer storage section for detecting the light quantity are provided together for measuring the pH and the light quantity simultaneously is shown in FIG. 12. In the circuit configuration, nine transistors and nine input and output wirings are necessary in one sensing section.

The sensing section, the transistors and the input and output wirings constituting the pH detecting device described above are integrated on the silicon substrate. So, such the integration can be realized easily to output the pH distribution as an image.

Figure 13:
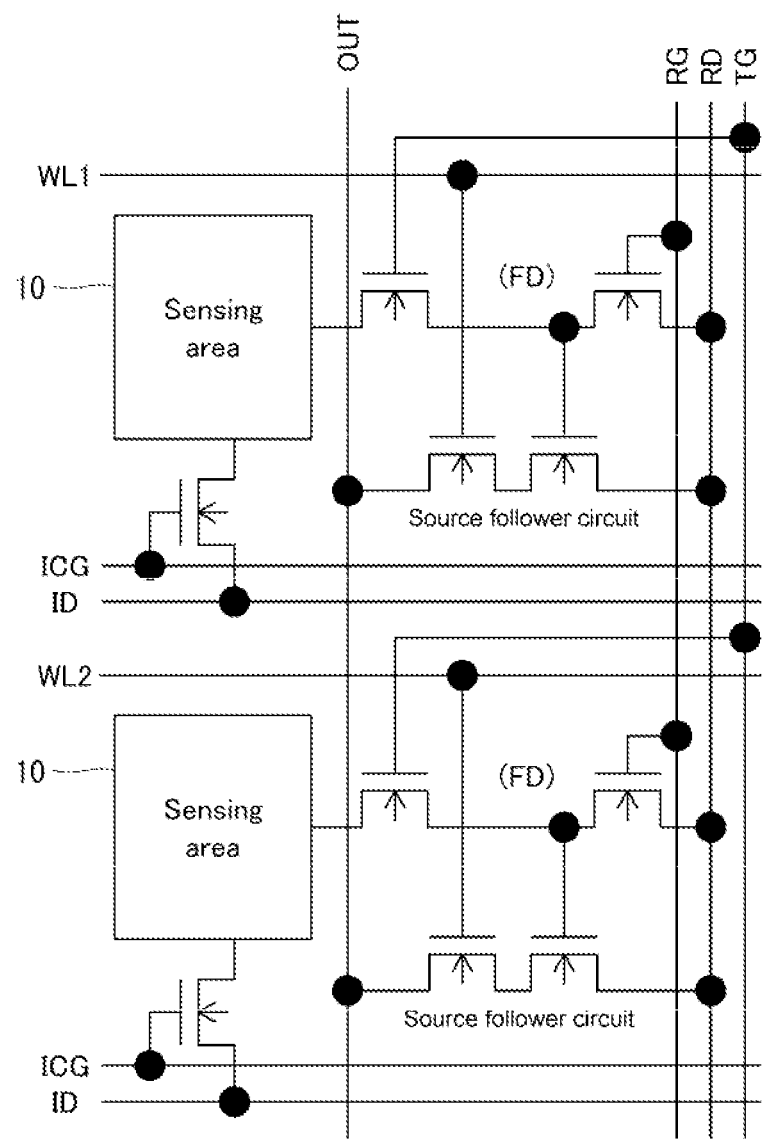
FIG. 13 is a basic circuit diagram of the integrated pH detecting devices.

The basic circuit configuration of the integrated pH detecting device is shown in FIG. 13. Similarly to the example of FIG. 11, in the example of FIG. 13, one sensing section, five transistors and seven input and output wirings are required per pixel.

Thus, a number of elements required per pixel prevent high integration.

So, the method for reducing the number of the transistors and the wirings, miniaturizing and integrating the pixels sophisticatedly are explained in the following.

(High Integration)

Figure 14:
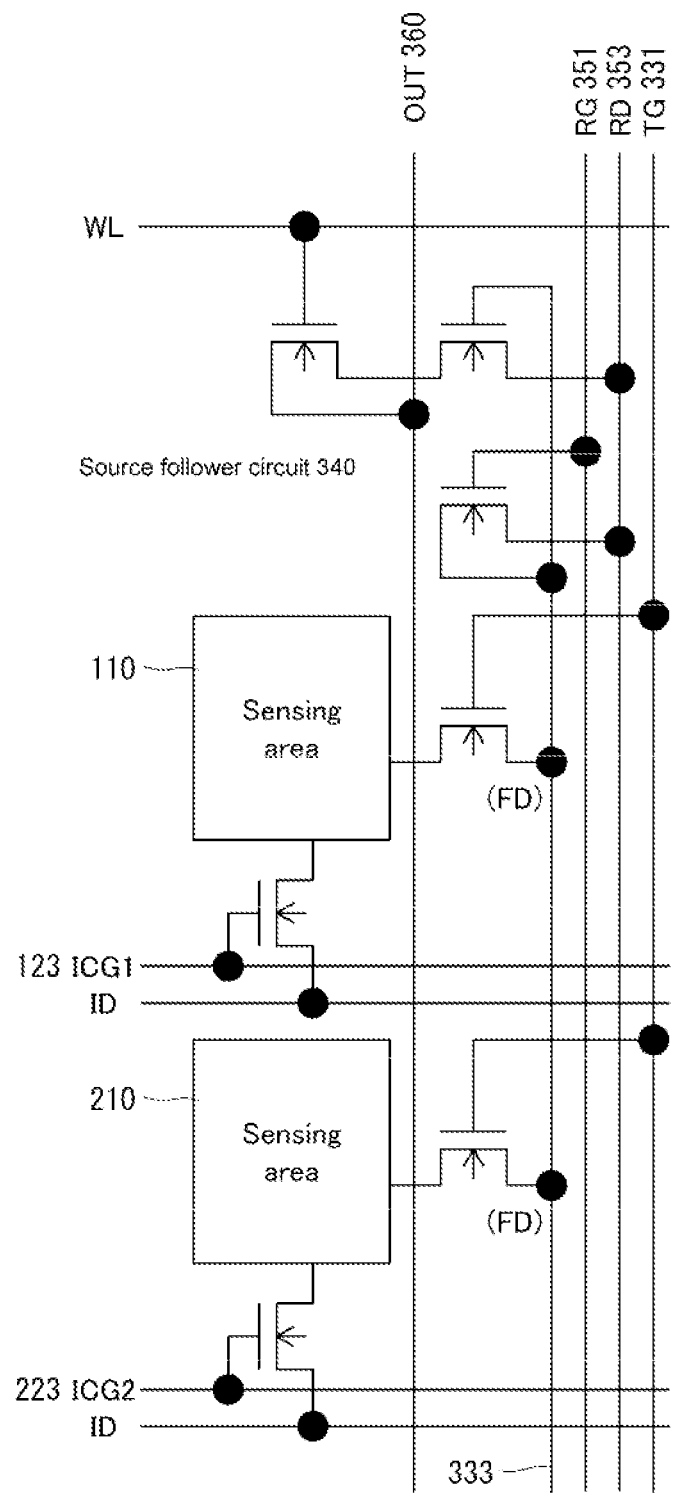
FIG. 14 is a circuit diagram suited for the high integration.

The example of the circuit configuration suited for high integration is shown in FIG. 14.

In such the circuit configuration, the FD section 333 of the first sensing section 110 and the second sensing section 210, the source follower circuit 340 for the charge quantity detecting section, the RG section 351, the RD section 353, the TG section 331 and the output wiring 360 are shared in common.

The TG section 331 is shared in common. So, the charge transfer from the first sensing section 110 and the second sensing section 210 to the RD section 331 is always executed at the same timing. In other words, the charge cannot be transferred to the FD section 333 by selecting each charge of the sensing sections 110, 210.

Accordingly, the sensing section 110 or 210 is selected by using the transistor provided for the sensing sections 110 and 210 except the TG section 331, namely by using the transistor for the ICG sections 123 and 223. In other words, when the TG section 331 is read out, the charge is put only in the sensing section 110 or 210 which is to be selected. So, either the charge is supplied only for the sensing section 110 or 210 which is to be selected, or the charge is evacuated from the non-selected sensing section to the ID sections 121 and 221 for emptying the charge of the non-selected sensing section after the charge is temporarily supplied for both of the sensing sections 110 and 210

In the circuit configuration shown in FIG. 14, three transistors and five input and output wirings shared in common are required. On the other hand, one sensing section, two transistors and two input and output wirings are required per pixel. Namely, as the integration level becomes higher, the number of transistors and input and output wirings required per pixel can be reduced.

Figure 15:
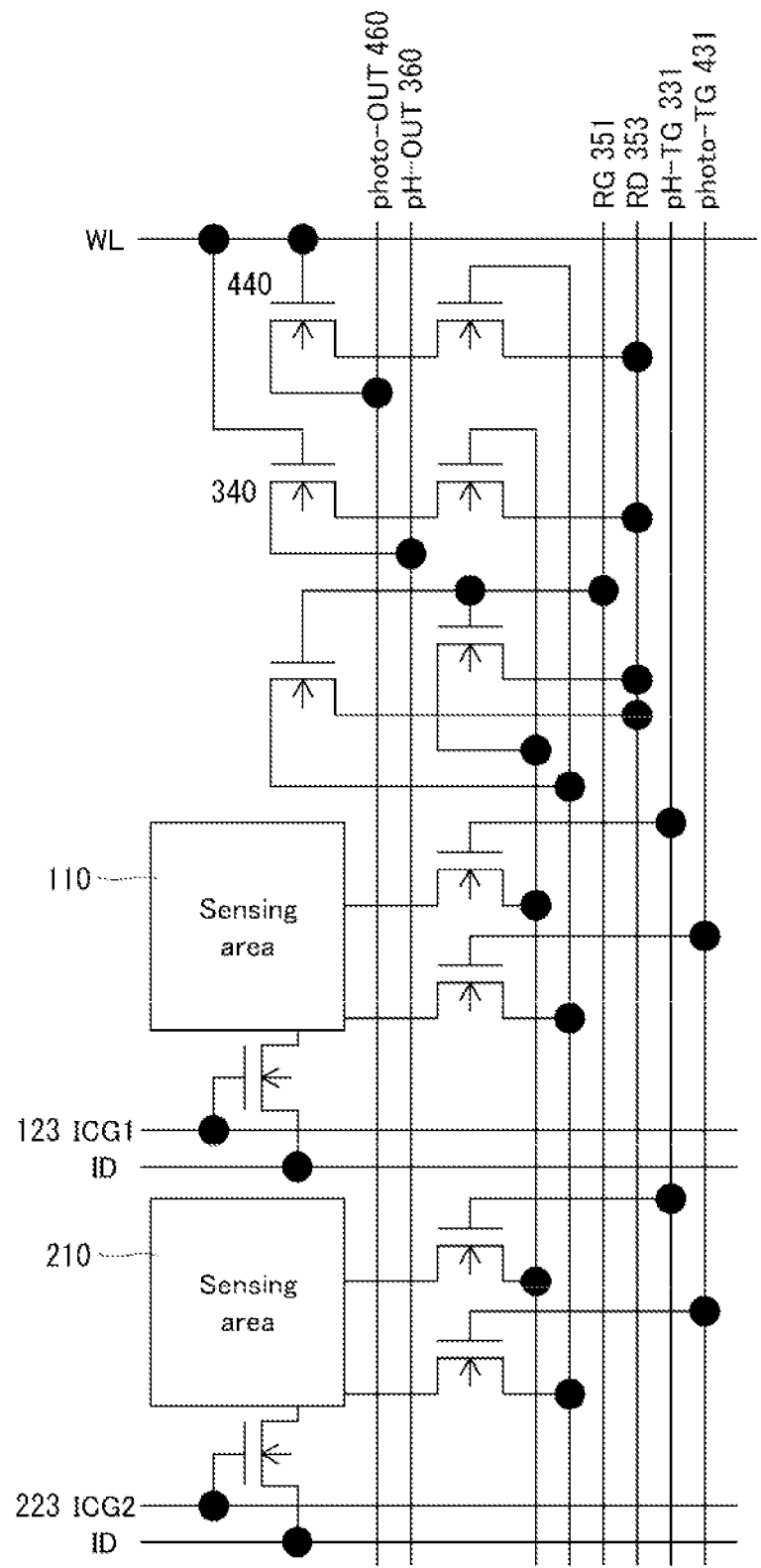
FIG. 15 is a circuit diagram of the charge transfer storage section for detecting pH and the charge transfer storage section for detecting light quantity which are suited for the integration.

FIG. 15 shows an example of a circuit configuration that a detecting device is provided with a charge transfer and storage section for detecting pH and a charge transfer and storage section for detecting light quantity. Such the example of the circuit configuration is suited for integration.

Incidentally, the same element as that of FIG. 14 is referred to the same reference numeral as that of FIG. 14 and the description thereof is eliminated.

In the example, the FD section 333 of the first sensing section 110 and the second sensing section 210, the source follower circuits 340, 440 for the charge quantity detecting section used for detecting pH and light quantity respectively, the RG section 351, the RD section 353, the TG section for pH 331, the TG section for light quantity 431, the output wiring for pH 360 and the output wiring for light quantity 470 are shared in common.

The detecting device for detecting pH executes the same operation as that of FIG. 14.

In the detecting device for detecting the light quantity, the charge is transferred from the sensing sections 110, 210 to the FD section 333 simultaneously. So, the first sensing section 110 and the second sensing section 210 are regarded as one sensing section. Preferably, the sensing sections are positioned as nearly as possible. For example, the sensing sections are preferably provided symmetrically to the input and output wirings of the RG section 351, the RD section 353 and the TG section 331.

In the descriptions above, a pH detecting device is explained as an example of a detecting device. With the selected sensing film, any of chemical and physical phenomena may be applied to the detected object.

The present invention is not limited to the illustrated embodiments or examples alone, but may be changed or modified within the scope of easily devised by those skilled in the art without departing from the spirit of the present invention.

The contents of the related art documents cited in the present specification are incorporated herein by reference as the content of the present specification.

Embodiments of chemical and physical phenomenon detecting devices described above are described in the following items (9)-(15).

(9) A chemical and physical phenomenon detecting device comprising:

a first sensing section and a second sensing section for changing each bottom potential of each potential well correspondingly to a chemical and physical phenomenon which is to be detected;

an FD section for storing each charge transferred at least from the first sensing section and the second sensing section through a TG section correspondingly at least to the first sensing section and the second sensing section and for identifying the chemical and physical phenomenon on a basis of the charge stored in the FD section; and a control section for changing a capacitance of a potential well of at least one of the first sensing section and the second sensing section for detecting the chemical and physical phenomenon, and/or changing a potential of the TG section for transferring the charge to transfer a first quantity of charges from a first potential well of the first sensing section and a second potential well of the second sensing section to the FD section correspondingly to the first sensing section and the second sensing section, when the chemical and physical phenomenon is in a first state of the chemical and physical phenomenon.

(10) A chemical and physical phenomenon detecting device according to (9),
wherein
the control section changes the capacitance of each potential well by changing a height of a potential barrier constituting each potential well.

(11) A chemical and physical phenomenon detecting device according to (9),
wherein
the control section changes the capacitance of each potential well by changing a bottom potential of each potential well.

(12) A chemical and physical phenomenon detecting device according to (11),
wherein
the control section changes the bottom potential of the potential well by a reference electrode.

(13) A chemical and physical phenomenon detecting device according to (9), comprising:
a second control section for setting a minimum height of a potential barrier constituting the first potential well the same as a minimum height of a potential barrier constituting the second potential well to detect a third charge quantity transferred from the first potential well to the FD section and a fourth charge quantity transferred from the second potential well to the FD section, when the chemical and physical phenomenon is in the first state of the chemical and physical phenomenon; and a third control section for changing the capacitance of the potential well and/or the potential of the TG section on a basis of the third charge quantity and the fourth charge quantity.

(14) A chemical and physical phenomenon detecting device according to (13), comprising:

a fourth control section for classifying the third charge quantity and the fourth charge quantity into predetermined charge quantity ranges and changing the capacitance of the potential well and/or the potential of the TG section on a basis of the predetermined charge quantity ranges.

(15) A chemical and physical phenomenon detecting device comprising:

a first sensing section and a second sensing section for changing each bottom potential of each potential well correspondingly to a chemical and physical phenomenon which is to be detected;

an FD section for storing each charge transferred at least from the first sensing section and the second sensing section through a TG section correspondingly at least to the first sensing section and the second sensing section and for identifying the chemical and physical phenomenon on a basis of the charge stored in the FD section; and a fifth control section for changing each sensing period of a first potential well of the first sensing section and a second potential of the second sensing section to transfer a first quantity of charges from the first potential well of the first sensing section and the second potential well of the second sensing section to the FD section correspondingly to the first sensing section and the second sensing section, when the chemical and physical phenomenon is in a first state of the chemical and physical phenomenon.

DESCRIPTIONS OF THE REFERENCE NUMERALS

1 pH detecting device
10 Sensing section, 12 Sensing film, 13 Reference electrode, 15 Potential well
20 Charge supply section, 21 ID section, 23 ICG section
30 Charge transfer storage section, 31 TG section, 33 FD section
40 Charge quantity detecting section
50 Charge eliminating section, 51 RG section, 53 RD section
71 Substrate, 72 p diffusion region, 73 n region, 74, 75, 77 n+ region

The invention claimed is:

1. A calibrating method for calibrating an output of each of detecting devices integrated with each of reference electrodes applied with a predetermined potential in an integrated device, each of the detecting devices comprising a sensing section for changing a bottom potential of a potential well correspondingly to a chemical and physical phenomenon to be detected, an ID section for supplying a charge to the sensing section, an ICG section for adjusting a charge quantity supplied from the ID section to the sensing section, and an FD section for storing a charge of the sensing section through a TG section, comprising:

a detecting step for detecting the output of each of the detecting devices correspondingly to a chemical and physical phenomenon of a standard state;

a comparing step for comparing the output of each of the detecting devices with a standard output of a standard detecting device corresponding to the chemical and physical phenomenon of the standard state; and a control step for changing a capacitance of a potential well of each of the detecting devices and/or changing a potential of the TG section in transferring the charge on a basis of a compared result of the comparing step to make the output of each of the detecting devices identical with the standard output.

2. A calibrating method according to claim 1, including a step of defining a minimum output among outputs of the detecting devices as the standard output.

3. A calibrating method according to claim 1, including a step of changing the capacitance of the potential well of each of the detecting devices by changing a potential height constituting the potential well of each of the detecting devices.

4. A calibrating method according to claim 3, including a step of controlling the potential height of the ICG section.

5. A calibrating method according to claim 1, including a step of changing the capacitance of the potential well by changing the bottom potential of the potential well.

6. A calibrating method according to claim 1, including steps of:

classifying the output of each of the detecting devices into predetermined output ranges; and changing the capacitance of the potential well of each of the detecting devices and/or changing the potential of the TG section on a basis of the output ranges.

7. A calibrating method for calibrating an output of each of detecting devices integrated with a reference electrode applied with a predetermined potential in an integrated device, each of the detecting devices comprising a sensing section for changing a bottom potential of a potential well correspondingly to a chemical and physical phenomenon to be detected, an ID section for supplying a charge to the sensing section, an ICG section for adjusting a charge quantity supplied from the ID section to the sensing section, and an FD section for storing a charge of the sensing section through a TG section, comprising:

a detecting step for detecting the output of each of the detecting devices correspondingly to a chemical and physical phenomenon of a standard state;

a comparing step for comparing the output of each of the detecting devices with a standard output of a standard detecting device corresponding to the chemical and physical phenomenon of the standard state; and a step for controlling a sensing period of each of the detecting devices on a basis of a compared result of the comparing step to make the output of each of the detecting devices identical with the standard output.

8. A calibrating device for calibrating an output of each of detecting devices integrated with a reference electrode applied with a predetermined potential in an integrated device, each of the detecting devices comprising a sensing section for changing a bottom potential of a potential well correspondingly to a chemical and physical phenomenon to be detected, an ID section for supplying a charge to the sensing section, an ICG section for adjusting a charge quantity supplied from the ID section to the sensing section, and an FD section for storing a charge of the sensing section through a TG section, comprising:

a detecting section for detecting the output of each of the detecting devices correspondingly to a chemical and physical phenomenon of a standard state;

a comparing section for comparing the output of each of the detecting devices with a standard output of a standard detecting device corresponding to the chemical and physical phenomenon of the standard state; and a control section for changing a capacitance of a potential well of each of the detecting devices and/or changing a potential of the TG section in transferring the charge on a basis of a compared result of the comparing section to make the output of each of the detecting devices identical with the standard output.

9. A calibrating device according to claim 8, wherein a minimum output is defined as the standard output among outputs of the detecting devices.

10. A calibrating device according to claim 8, wherein the control section changes the capacitance of the potential well of each of the detecting devices by changing a potential height constituting the potential well of each of the detecting devices.

11. A calibrating device according to claim 10, wherein the control section changes the potential height constituting the potential well of each of the detecting devices by changing a potential of the ICG section.

12. A calibrating device according to claim 8, wherein the control section changes the capacitance of the potential well of each of the detecting device by changing the bottom potential of the potential well of each of the detecting devices.

13. A calibrating device for calibrating an output of each of detecting devices integrated with a reference electrode applied with a predetermined potential in an integrated device, each of the detecting devices comprising a sensing section for changing a bottom potential of a potential well correspondingly to a chemical and physical phenomenon to be detected, an ID section for supplying a charge to the sensing section, an ICG section for adjusting a charge quantity supplied from the ID section to the sensing section, and an FD section for storing a charge of the sensing section through a TG section, comprising:

a detecting section for detecting the output of each of the detecting devices correspondingly to a chemical and physical phenomenon of a standard state;

a comparing section for comparing the output of each of the detecting devices with a standard output of a standard detecting device corresponding to the chemical and physical phenomenon of the standard state; and a control section for controlling a sensing period of each of the detecting devices on a basis of a compared result of the comparing section to make the output of each of the detecting devices identical with the standard output.

* * * * *